(12) United States Patent
Kita

(10) Patent No.: US 6,641,589 B2
(45) Date of Patent: Nov. 4, 2003

(54) OPHTHALMIC SURGICAL LENS

(76) Inventor: Kiyoshi Kita, 4-4-7-502 Honmachi, Shibuya-ku, Tokyo 151 (JP)

( * ) Notice: Subject to any disclaimer, the term of this patent is extended or adjusted under 35 U.S.C. 154(b) by 0 days.

(21) Appl. No.: 09/968,806

(22) Filed: Oct. 3, 2001

(65) Prior Publication Data

US 2003/0014106 A1 Jan. 16, 2003

(30) Foreign Application Priority Data

Jul. 16, 2001 (JP) ........................................ 2001-248365

(51) Int. Cl.[7] ................................................. A61F 9/00
(52) U.S. Cl. ............................. 606/107; 606/4; 606/5; 623/6; 623/4; 351/160 R; 351/160 H; 351/161; 351/162; 351/177
(58) Field of Search ............................... 623/6.11, 6.38, 623/6.43, 6.44, 6.51, 6.56, 5, 4.1, 6; 606/107, 4, 5; 351/160 R, 160 H, 161, 162, 177

(56) References Cited

U.S. PATENT DOCUMENTS

| 4,406,285 A | 9/1983 | Villasenor et al. |
|---|---|---|
| 4,572,182 A | 2/1986 | Royse |
| 4,990,150 A | 2/1991 | Tsubota et al. |
| 5,021,057 A | 6/1991 | Byrne, Jr. |
| 5,951,565 A | * 9/1999 | Freeman ..................... 606/107 |
| 6,461,384 B1 | * 10/2002 | Hoffmann et al. ......... 623/6.51 |

OTHER PUBLICATIONS

"Incidence, Risk Factors, and Morphology in Operating Microscope Light Retinopathy", American Journal of Ophthalmology, vol. 103, Mar. 1997 (pp. 255–263).

* cited by examiner

Primary Examiner—David J. Isabella
Assistant Examiner—Kamrin Landrem
(74) Attorney, Agent, or Firm—Staas & Halsey, LLP

(57) ABSTRACT

An ophthalmic surgical lens to prevent retinopathy caused by microscopic illumination during cataract or intra-ocular lens surgery. The lens is soft and includes a transparent lens portion placed on a cornea, at least one haptic that extends from the base of the lens portion, and at least one aperture formed by the at least one haptic and the base of the lens portion. The at least one aperture exposes the ocular surface to allow for surgical incisions. The lens portion prevents incisions from being made on the cornea during surgery. The lens also absorbs a patient's corneal refraction so as to prevent the retinopathy.

31 Claims, 2 Drawing Sheets

OPHTHALMIC SURGICAL LENS

CROSS REFERENCE TO RELATED APPLICATION

This application claims the benefit under 35 U.S.C. Section 119 of Japanese Patent Application Serial No. 2001-248365, filed Jul. 16, 2001, which is hereby incorporated by reference in its entirety into this application.

BACKGROUND OF THE INVENTION

1. Field of the Invention

The invention relates to an ophthalmic surgical contact lens which is used especially in cataract and intra-ocular lens (IOL) implant surgeries.

2. Description of the Related Art

Cataract and IOL implant surgeries are effective in the treatment of cataract and are used for refractive correction in ophthalmology. Such surgeries are performed under a surgical microscope.

More particularly, a coaxial illumination of the surgical microscope is focused on the ocular fundus of a patient's eye to improve a surgeon's visibility. It has been found that such microscopic light during surgery, however, can be harmful, causing what is known as operation microscope retinopathy (e.g., erythropia) or retinal photo-toxicity. For example, the Japanese magazine "Ophthalmology MOOK" No. 47, 1992, pages 131–145, reports that the occurrence of such retinopathy is as high as 35%, and the U.S. magazine "American Journal of Ophthalmology", vol. 103, 1987, pages 255–263, reports 7.4%. Thus, these magazines conclude that such retinopathy is of significant concern.

The following methods have been used in an attempt to prevent this retinopathy, and visual acuity reduction in patients: oblique illumination, a light-filter or a light-shield on the cornea. Usually, the light-shield is chosen from a sponge, a light-shield lid or a black contact lens.

Further, a patient's cornea is exposed to air during cataract and IOL-implant surgeries. That is, the patient's eyelids are kept open with a speculum during the surgery, so the patient cannot blink. The surgeon must keep the patient's eye wet during the surgery.

Generally, continuous circular capsulotomy is performed in cataract surgery. It is a very delicate operation, and occasionally the surgeon may tear an equator of the lens capsule, or scratch the cornea. The disruption of the lens capsule or distorted capsulotomy may lead to mispositioning of an IOL that is subsequently implanted in the capsule.

There are many diagnostic and surgical lenses for ophthalmic uses. Surgical lenses are used mainly for iridectomy, trabeculectomy, vitrectomy, retinal detachment surgery, goniotomy, expulsive choroidal hemorrhage surgery, etc. The diagnostic uses are for observing the gonio angle, iris, vitreous cavity, ocular fundus, etc. The optical shapes of these ophthalmic surgical lenses are typically plano-concave, bi-concave, convex-concave (meniscus) and prism-concave.

U.S. Pat. No. 5,021,057 discloses a relatively hard lens intended to help stop the effusion of ocular material in the event of expulsive choroidal hemorrhage during anterior segment surgery. The lens is placed over the incision to block flow from the eye. The patent also discloses a radial slot in the lens that allows suturing to close an incision while pressure is applied to the eye globe. The device must be rotated to create more than one suture.

SUMMARY OF THE INVENTION

It is a purpose of the present invention to prevent corneal disorder in a patient by avoiding corneal scratches caused by surgical instruments, prevent corneal physiological malfunction caused by air, and provide a continuous presence of ophthalmic solution during ophthalmic surgery.

It is another purpose to provide an ophthalmic surgical lens that leads to more successful cataract surgery and/or IOL implant surgery.

It is still another purpose to provide a lens that reduces a patient's corneal refractive power during surgery, while dispersing microscopic illumination on a patient's ocular fundus.

It is another purpose to provide an ophthalmic surgical lens to be placed on a patient's cornea, which lens is effective in preventing operation microscope light retinopathy, and avoiding damage to the cornea due to incisions being made during surgery.

It is also a purpose to provide a surgical lens that can be used during the entire surgical procedure.

It is another purpose of the present invention to provide a surgical lens which facilitates the immediate removal of a luxated cataractous lens or an IOL, both captured in the vitreous cavity, during cataract or IOL implant surgery.

To achieve the foregoing and other purposes of the present invention there is provided a surgical lens, including a lens portion having a concave surface that simulates a human corneal surface, at least one haptic that extends from or supports the lens, and at least one aperture adjacent the haptic. The at least one aperture exposes the ocular surface so that an incision can be made therein, but the lens portion protects the cornea. Several apertures may be needed in the area within the over-all length of the lens, depending on the types of surgery.

The lens is preferably made of a soft material selected from silicones, acrylic resins and plastics. The periphery of the lens surface or the haptic surface is preferably a circle for use in regular ophthalmic surgeries.

A small amount of viscous ophthalmic solution, such as sodium hyaluronate solution, condroitin sulfate solution or methyl cellulose solution, is applied on the surface which is placed on the patient's cornea. The corneal surface is thus separated from the air by the ophthalmic solution.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 1:
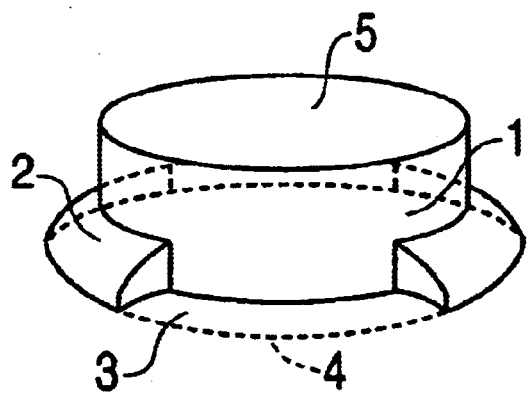
FIG. 1 illustrates a perspective view of a first embodiment of the lens of the present invention.

FIG. 1 is a perspective view of the surgical lens of the present invention used preferably for cataract or IOL implant surgery, but also for surgery involving the posterior segment of the eye globe, if needed. The lens includes a lens portion 1, at least one haptic or flange 2 extending from a base of the lens portion 1, and supporting the lens portion 1, and at least one aperture 3 adjacent the at least one haptic 2. The number of apertures 3 corresponds to the number of haptics 2. In this embodiment, two haptics 2, and two apertures 3, are used. However, as desired for particular types of ophthalmic surgeries, more than two haptics 2/apertures 3 can be used, generally symmetrical about the lens portion 1.

The lens can be made of hard materials such as glass or rigid plastics, or soft materials, which is preferable, such as silicones, acrylic resins or soft plastics.

At least the lens portion 1 of the lens of the present invention should be transparent.

Figure 4:
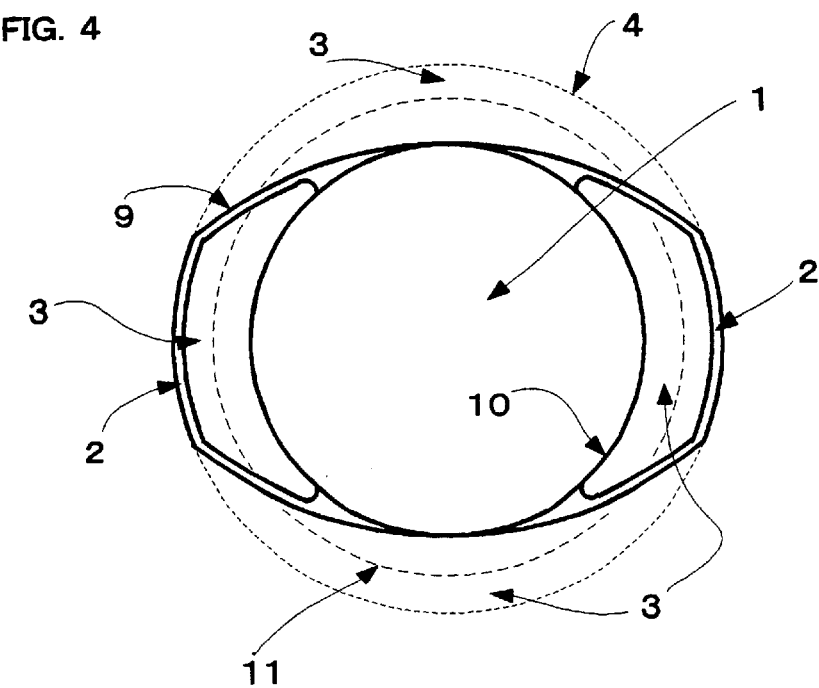
FIG. 4 illustrates a top plan view of a second embodiment of the lens of the present invention, in relation to a cornea.

The haptic 2 can take the form of a solid plate or extension, such as shown in FIG. 1, a loop, as shown in FIG. 4, or other shapes, as desired.

Each aperture 3 is formed within an area of over-all length or diameter 4 of the surgical lens. The aperture 3 is provided to allow incisions to be made during surgery. Such incisions are usually made up to the pars plana, avoiding the pupil area of the cornea. In other words, incisions will be made from approximately 3 mm distal in a radial direction from the corneal apex, to approximately 3 mm distally on the sclera from the corneal limbus.

Figure 2:
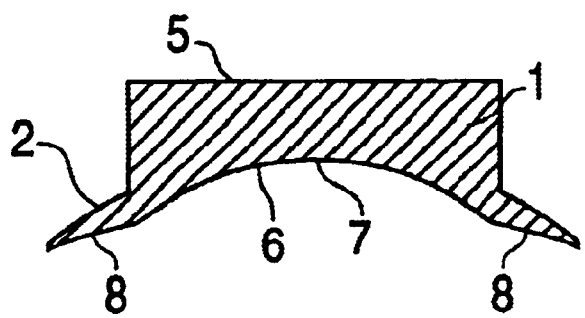
FIG. 2 illustrates a cross sectional side view of the lens shown in FIG. 1.

Referring specifically to FIG. 2, an upper surface 5 of the lens portion 1 is intended to face a microscope, and a bottom surface 6 is placed on a patient's cornea, so that a lens optical axis' crossing point 7 corresponds with the patient's corneal axis. The bottom surface 6 of the lens is concave to simulate a radius of a human cornea, and should be a minimum of approximately 6 mm in width (i.e. in diameter).

Any space between the radii of the bottom surface 6 and the patient's cornea may be filled with a ophthalmic solution, such as sodium hyaluronate, condroitin sulfate, or methyl cellulose solution.

The surgical lens of the present invention should not be pressed hard on the cornea. It can follow the shape of corneal surface 12 (FIG. 5), if it is made of a soft material, and shows good adhesion to the corneal surface 12 during surgery.

Figure 5:
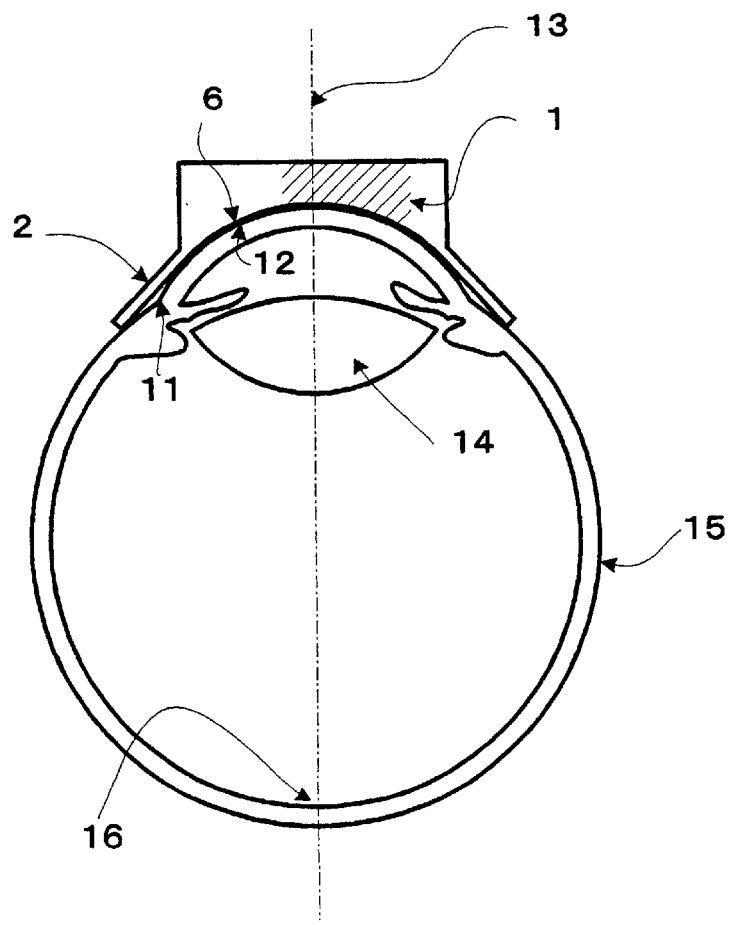
FIG. 5 illustrates a side-cross sectional view of the lens shown in FIG. 4.

Surface 8 underneath the haptics 2 may be concave to simulate a human scleral radius (for instance, approximately 10–11 mm), or be straight to mimic an angle of a tangent line of the sclera of an eye globe 15 (see the haptics 2 of FIG. 5). The angle may be determined by the width (diameter) of the concave surface 6.

The optical configuration of the lens of the present invention includes shapes selected from plano-concave, bi-concave, convex-concave (meniscus) and prism-concave.

In order to align the lens' optical axis and the center of gravity, the surgical lens of the present invention preferably uses symmetric shapes. The shape may be selected from the group of oval, ovoid, rhombus, butterfly, triangle, quadrangle, polygon, star-burst or gear-like.

The center of gravity of the lens is preferably within approximately 3 mm from the optical axis 7 of the lens, except a prism-concave type. Even if the lens were not a symmetric configuration, the lens is not likely to slip off from its proper position, when the center of gravity is within approximately 3 mm from the visual axis of the eye.

Figure 3:
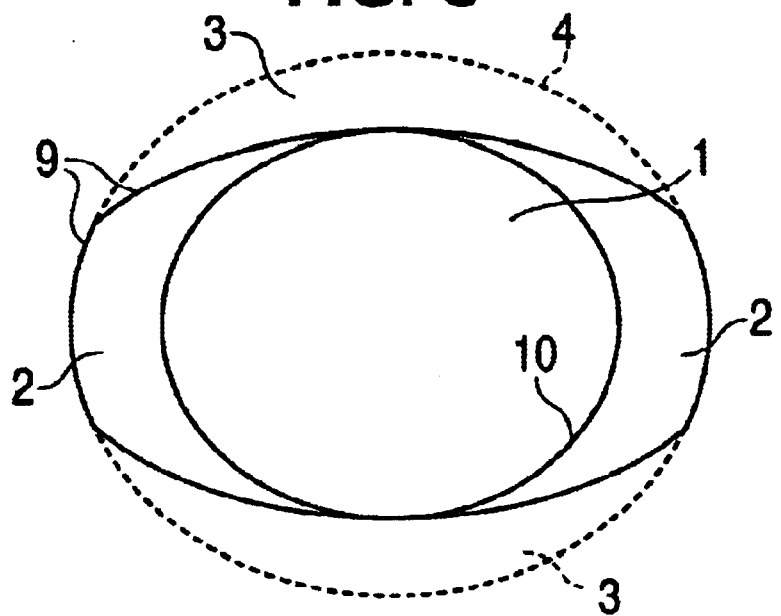
FIG. 3 illustrates a top plan view of the lens shown in FIG. 1.

FIG. 3 illustrates the surgical lens of the present invention, shown in FIGS. 1 and 2, placed on a cornea. As seen, the surface 6 that is placed on the cornea has a concave configuration to simulate the human corneal surface.

The two apertures 3 are formed within the area of the over-all length or diameter 4 of the lens. A periphery 9 of the overall lens or the haptics 2 simulates an ovoid shape. In contrast, the periphery 10 of the lens portion 1 preferably resembles a circular periphery of a cornea. However, the surface 6 of the lens that contacts the cornea can be made smaller than the cornea, and does not have to be a circle. Each aperture 3 is again provided on the ocular surface to allow incisions to be made during surgery.

FIG. 4 shows a second embodiment of a surgical lens of the present invention wherein a lens portion 1 is placed on a cornea and two haptics 2 extend from and support the lens portion 1. The surface 6 that is placed on the cornea is again concave to simulate a human corneal surface, and the periphery 9 of at least either the lens portion 1 or the haptics 2 preferably is a circle.

Two apertures 3 expose a portion of the ocular surface, as in the FIG. 3 embodiment above. However, the haptics 2 in this embodiment are of a loop configuration. That is, two additional apertures 3 are formed within the periphery 9, so that four total apertures 3 are provided within the area of over-all length 4. These four apertures 3 are all provided for incisions to be made therein during surgery. The incisions can be made substantially anywhere around the corneal limbus 11.

The periphery 10 of lens portion 1 facing the cornea is smaller than the corneal limbus 11 as shown. The periphery 10 of lens portion 1 in this embodiment is a circle.

Relative to FIG. 5, if the surgical lens described above were not used, an irradiated microscope illumination of the cornea passing through the surface 12 and a crystalline lens 14, would focus on the fundus of the eye globe 15. The visual axis 13 shares an optical axis of the lens, which is in common with a macula 16 having a high visual sensitivity. The refractive power of the corneal surface 12 exposed to the air, is approximately 40 diopters (D), and the crystalline lens 14 is approximately 20 D. This means that the eye globe 15 includes a strong convex lens. It is well known that retinal disorder occurs immediately if we look at the sun directly. The surgical illumination acts like the sun, even if the volume of illumination were much less. Generally the microscopic illumination is aligned to be coaxial to the optical and visual axes. In cataract, the crystalline lens 14 decreases the incoming volume of light and results in lesser illumination to the macula 16.

Right after the cataractous lens 14 is removed from the eye, nothing shields incoming light, so that the macula 16 receives the focused strong microscope illumination. Such strong refractive power (approx. 40 D) at the cornea 12 is focused on the patient's fundus. From this moment the surgeon must be very cautious to avoid photo-toxicity of the macula 16.

Following an IOL implantation, the dangers connected with operation microscope light retinopathy of a patient are increased. That is to say, incoming strong light is more focused on the retina, increasing photo-chemical reaction and temperature elevation in the retina.

This potential operation retinopathy can be prevented by placing the above-described surgical lens' concave surface 6 (radius approximately 7 to 10 mm, and typically approximately 8 mm) on the corneal surface 12 so as to correspond to an optic axis of the lens' and the visual axis 13, as shown in FIG. 5. In other words, the surgical lens of the present invention absorbs the refractive power of approximately 40 D at the corneal surface 12. If the lens of the present invention were a plano-concave type, depending on a refractive index of the material, it diffuses the light from the cornea to the crystalline lens 14. The light diffused by the lens portion 1 does not focus on the macula 16 even with a clear cornea, a clear crystalline lens or an IOL therebetween. Photo-toxicity at the macula 16 can be prevented with the use of the surgical lens of the present invention.

Furthermore, anterior capsulotomy and an extraction of cataractous crystalline lens 14 can be performed easily by absorption of the refractive power of the corneal surface 12. And, the patient's fundus can be observed with a simple manipulation of the microscope focusing knob.

EXPERIMENT 1

A microscopic illumination test was performed using a fresh pig eye enucleated after death. A soft silicone lens (a plano-concave type as shown in FIG. 1, with a radius of the concave surface of 8 mm, a refractive index of 1.4, and an over-all length 4 of 14 mm) was used. A small amount of viscous material, a sodium hyaluronate solution, was put on the concave surface of the lens and placed on a pig eye to align an optical axis of the lens and an apex of the pig cornea. Using this eye, the following experiments were performed.

The sclera of the posterior segment of the pig eye was exposed, and the eyeball was fixed cornea-side up in a petri dish containing a saline solution of about 10 mm in depth. Then, the surgical lens according to the present invention was placed on the pig cornea, and a strong microscope illumination was irradiated on the pig cornea in a dark room. The sclera was observed through the bottom of the dish. A dim spot of about 10 mm in diameter was observed on the bottom of the sclera. Then the lens was removed from the pig eye and the sclera was observed again after a good rinsing of the cornea. The dim spot was about 3 mm in diameter this time. The difference was significant, even when considering errors in pupil size, the refractive power of the pig eye, the lens phenomenon of the dish, and the settings of the microscope.

EXPERIMENT 2

Microscopic observation was performed with the condition described above for EXPERIMENT 1. The differences between using the lens on the cornea and not using the lens on the cornea, were observed by focusing the microscope on a pig iris. The pupil size was approximately 1 mm smaller in width when the lens was used, than without the lens. Although the tip of a cystotome was inserted through a corneal limbal incision into the pig eye on the iris, the lens kept sticking to the cornea, even though the corneal incision was enlarged and moved up a bit. It seemed that the cystotome manipulation had no sense of incongruity, whether using the lens or not. Other than operation microscope light retinopathy, it is suggested that an easier manipulation of the instruments can be expected with the use of the lens of the present invention since the corneal 40 D refraction can be ignored.

Then, focusing the microscope on the ocular fundus of the pig eye, the fundus was observed with and without the lens. The optic disc and blood vessels were clearly observed with the use of the lens, but not observed without the lens.

The use of the lens of the present invention absorbs a patient's strong corneal refractive power, thereby preventing operation microscope light retinopathy and visual loss due to a microscope illumination during cataract or IOL implant surgery, and presenting easier intra-ocular manipulation of the instruments during cataract and IOL implant surgeries. Also the use of the lens of the present invention isolates the patient's cornea from the air, and prevents damage to the cornea from instruments used during surgery.

Also, when a surgeon uses the surgical lens of the present invention on a patient's cornea, it should lead to easier capsulotomy and an IOL insertion in the capsular bag for the surgeon. The surgeon can observe, through the lens under a microscope, the torn edge of the capsule and the IOL, naturally without distortion due to a strong corneal refraction. Furthermore, the surgeon can observe the patient's ocular fundus through the transparent lens, when the surgeon focuses the microscope on the fundus.

The lens of the present invention can be used with both anterior and posterior segment surgeries to prevent operation microscope light retinopathy and visual reduction. In addition, the surgeon can naturally observe the patient's retina and transparent bodies such as the aqueous humor, crystalline lens, an implanted IOL and the vitreous body during the surgery. Furthermore, if a crystalline lens or an IOL is captured in the vitreous cavity during surgery, an immediate operation can be performed with the use of the lens of the present invention. These attributes contribute to the patient's visual acuity, minimize the patient's risk, and facilitate surgery.

The foregoing is considered illustrative only of the principles of the invention. Further, since numerous modifications and changes will readily occur to those skilled in the art, it is not desired to limit the invention to the exact construction and operation shown and described. Accordingly, all suitable modifications and equivalents may be resorted to that fall within the scope of the invention and the appended claims.

What is claimed is:

1. A surgical lens to prevent retinopathy caused by microscope illumination during ophthalmic surgery, which surgical lens is placed on a patient's eye, over the cornea, comprising;

a transparent lens portion made of a soft material and having a concave surface simulating a human corneal surface, said concave surface to be placed over the cornea;

at least one haptic that is made of a soft material, extends from the lens portion, and has a surface for facing a human sclera that simulates a human scleral radius; and at least one aperture formed by the haptic and the lens portion to expose an exterior portion of the ocular surface within an over-all area defined by the lens, wherein only said surface of the lens portion and said surface of the at least one haptic contact the eye.

2. The surgical lens as recited in claim 1, wherein a periphery of the surgical lens is non-circular.

3. The surgical lens as recited in claim 1, wherein a periphery of the lens portion is circular.

4. The surgical lens as recited in claim 1, wherein the at least one haptic is two haptics positioned opposite each other relative to the lens portion.

5. The surgical lens as recited in claim 1, wherein the at least one haptic is a solid plate.

6. A surgical lens to prevent retinopathy caused by microscope illumination during ophthalmic surgery, which surgical lens is placed on a patient's eye, over the cornea, comprising;

a transparent lens portion having a concave surface simulating a human corneal surface, said concave surface to be placed over the cornea;

at least one haptic made of a soft material that extends from the lens portion; and at least one aperture formed by the haptic and the lens portion to expose an exterior portion of the ocular surface within an over-all area defined by the lens;

wherein the at least one haptic includes a surface which faces the sclera and simulates a human scleral radius.

7. The surgical lens as recited in claim 1, wherein a periphery of the lens is a shape selected from the group of oval, ovoid, rhombus, butterfly, triangle, quadrangle, polygon, star-burst and gear-like.

8. The surgical lens as recited in claim 1, wherein the surgical lens has an optical configuration selected from the group of piano-concave, bi-concave, meniscus and prism-concave.

9. The surgical lens as recited in claim 1, wherein the soft material is selected from silicones, acrylic resins and plastics.

10. A surgical lens for use in a cataract surgery or an intra-ocular lens implant surgery, comprising:

a transparent lens having a surface to be placed on an exterior surface of an eye, over the cornea, said lens surface having a concave radius between 7 and 10 mm and, a diameter of at least 6 mm, and a lens optical configuration selected from the group of piano-concave, bi-concave, meniscus and prism-concave, wherein only said surface of the lens contacts the eye.

11. A surgical lens, comprising;

a transparent lens portion made of a soft material and having a surface on a base that is concave to simulate a human corneal surface, said concave surface to be placed on an exterior surface of an eye, over the cornea;

at least two haptics, each of which is made of a soft material, extends from the base of the lens portion, and has a surface that faces a human sclera and simulates a human scleral radius; and at least two apertures, each of which is formed between each haptic and the base, wherein each aperture exposes an exterior portion of the ocular surface, wherein only said surface of the lens portion and said surface of the at least two haptics contact the eye.

12. The surgical lens as recited in claim 11, wherein each haptic further comprises an aperture therein.

13. The surgical lens as recited in claim 11, wherein the at least two haptics is three haptics, and the at least two apertures is three apertures.

14. The surgical lens as recited in claim 11, wherein a periphery of the lens is a shape selected from the group of circle, oval, ovoid, rhombus, butterfly, triangle, quadrangle, and polygon, star-burst and gear-like.

15. The surgical lens as recited in claim 11, wherein the lens has an optical configuration selected from the group of piano-concave, bi-concave, meniscus and prism-concave.

16. The surgical lens as recited in claim 11, wherein the soft material is selected from silicones, acrylic resins and plastics.

17. A method of performing ophthalmic surgery utilizing the surgical lens as recited in claim 11.

18. A surgical lens for allowing intra-ocular manipulation of instruments during cataract and intra-ocular lens implant surgeries, which surgical lens portion is placed over a patient's eye cornea, comprising:

a transparent lens portion made of one of a hard and a soft material, wherein a surface of the lens portion to be placed over the patient's cornea has a concave radius between 7 and 10 mm, a diameter of at least 6 mm, and a lens optical configuration selected from the group of plano-concave, bi-concave, meniscus and prism-concave;

wherein only said surface of the lens portion contacts the eye.

19. A surgical lens used to facilitate removal of a cataractous lens or an intra-ocular lens captured in a vitreous cavity in a patient during cataract or intra-ocular lens implant surgery, which surgical lens is placed over the patient's eye cornea, comprising;

a transparent lens portion made of one of a hard and a soft material, wherein a surface of the lens portion to be placed over the patient's cornea has a concave radius between 7 and 10 mm, a diameter of at least 6 mm, and a lens optical configuration selected from the group of plano-concave, bi-concave, meniscus and prism-concave, wherein only said surface of the lens portion contacts the eye.

20. The surgical lens as recited in claim 18, further comprising:

at least one haptic that extends from the lens portion; and at least one aperture formed by the haptic and the lens portion to expose an exterior portion of the ocular surface within an over-all area defined by the lens.

21. A surgical lens as recited in claim 19, further comprising:

at least one haptic that extends from the lens portion; and at least one aperture formed by the haptic and the lens portion to expose an exterior portion of the ocular surface within an over-all area defined by the lens.

22. A surgical lens for use in anterior segment surgery, during an entire surgical procedure, which lens is placed over a patient's eye cornea, comprising:

a transparent lens portion made of one of a hard and a soft material, wherein a surface of the lens portion to be placed over the patient's cornea has a concave radius between 7 and 10 mm, a diameter of at least 6 mm, and a lens optical configuration selected from the group of plano-concave, bi-concave, meniscus and prism-concave:

at least one haptic that extends from the lens portion; and at least one aperture formed by the haptic and the lens portion to expose an exterior portion of the ocular surface providing for surgical incisions, within an over-all area defined by the surgical lens;

wherein only said surface of the lens portion and the at least one haptic contact the eye.

23. The surgical lens as recited in claim 1, wherein the at least one haptic is a loop.

24. A surgical lens to prevent retinopathy caused by microscope illumination during ophthalmic surgery, which surgical lens is placed on a patient's eye, over the cornea, comprising;

a transparent lens portion having a concave surface simulating a human corneal surface, said concave surface to be placed over the cornea;

at least one haptic made of a soft material that extends from the lens portion; and at least one aperture formed by the haptic and the lens portion to expose an exterior portion of the ocular surface within an over-all area defined by the lens;

wherein the at least haptic includes a surface which faces the sclera and simulates an angle of a tangent line of the sclera.

25. A surgical lens to prevent retinopathy caused by microscope illumination during ophthalmic surgery, which surgical lens is placed on a patient's eye, over the cornea, a transparent lens portion having a concave surface simulating a human corneal surface, said concave surface to be placed over the cornea;

at least one haptic made of a soft material that extends from the lens portion; and at least one aperture formed by the haptic and the lens portion to expose an exterior portion of the ocular surface within an over-all area defined by the lens comprising;

a transparent lens portion made of a soft material and having a surface on a base that is concave to simulate a human corneal surface, said concave surface to be placed on the cornea;

at least two haptics, each of which is made of a soft material and extends from the base of the lens portion; and at least two apertures, and each of which is formed between each haptic and the base, wherein each aperture exposes a portion of the ocular surface, wherein the at least haptic includes a surface which faces the sclera and simulates an angle of a tangent line of the sclera.

26. The surgical lens as recited in claim 18, wherein the soft material is selected from silicones, acrylic resins and plastics.

27. The surgical lens as recited in claim 18, wherein the hard material is selected from glass and rigid plastics.

28. The surgical lens as recited in claim 19, wherein the soft material is selected from silicones, acrylic resins and plastics.

29. The surgical lens as recited in claim 19, wherein the hard material is selected from glass and rigid plastics.

30. The surgical lens as recited in claim 22, wherein the soft material is selected from silicones, acrylic resins and plastics.

31. The surgical lens as recited in claim 22, wherein the hard material is selected from glass and rigid plastics.

* * * * *

UNITED STATES PATENT AND TRADEMARK OFFICE
CERTIFICATE OF CORRECTION

PATENT NO.     : 6,641,589 B2                                           Page 1 of 1
DATED          : November 4, 2003
INVENTOR(S)    : Kiyoshi Kita It is certified that error appears in the above-identified patent and that said Letters Patent is hereby corrected as shown below:

<u>Column 7,</u>
Lines 17, 28 and 56, change "piano" to -- plano --.

Signed and Sealed this

Sixth Day of January, 2004

JAMES E. ROGAN
*Director of the United States Patent and Trademark Office*